(12) United States Patent
Gordon et al.

(10) Patent No.: US 9,659,760 B2
(45) Date of Patent: May 23, 2017

(54) AUTOMATED ADJUSTMENT OF CAPILLARY VOLTAGE BASED ON THE ELUTION CONDITIONS TO RETAIN OPTIMAL IONIZATION CONDITIONS

(71) Applicant: Micromass UK Limited, Wilmslow (GB)

(72) Inventors: David Gordon, Manchester (GB); Alexander Hooper, Stoke-on-Trent (GB); Daniel James Kenny, Knutsford (GB); Richard Barrington Moulds, Stockport (GB); David Pugh, Cheshire (GB); Kate Whyatt, Cheshire (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 15/022,576

(22) PCT Filed: Sep. 17, 2014

(86) PCT No.: PCT/GB2014/052821
§ 371 (c)(1),
(2) Date: Mar. 17, 2016

(87) PCT Pub. No.: WO2015/040388
PCT Pub. Date: Mar. 26, 2015

(65) Prior Publication Data
US 2016/0233071 A1    Aug. 11, 2016

(30) Foreign Application Priority Data
Sep. 20, 2013  (EP) .................................. 13185285
Sep. 20, 2013  (GB) .................................. 1316686.3

(51) Int. Cl.
*H01J 49/16*  (2006.01)
*H01J 49/00*  (2006.01)
*G01N 30/72*  (2006.01)

(52) U.S. Cl.
CPC ........ *H01J 49/167* (2013.01); *G01N 30/7266* (2013.01); *H01J 49/0031* (2013.01); *H01J 49/165* (2013.01)

(58) Field of Classification Search
CPC  G01N 30/7266; H01J 49/0031; H01J 49/165; H01J 49/167
See application file for complete search history.

(56) References Cited

U.S. PATENT DOCUMENTS 6,744,046 B2   6/2004  Valaskovic et al.
6,790,354 B1   9/2004  Moon et al.
(Continued)

FOREIGN PATENT DOCUMENTS

EP    0655769    5/1995

OTHER PUBLICATIONS

Karas, M., U. Bahr, and T. Dülcks. "Nano-electrospray ionization mass spectrometry: addressing analytical problems beyond routine." Fresenius' journal of analytical chemistry 366.6-7 (2000): 669-676.*

(Continued)

*Primary Examiner* — Wyatt Stoffa
(74) *Attorney, Agent, or Firm* — Diederiks & Whitelaw, PLC

(57) ABSTRACT

A method of Electrospray ionization is disclosed comprising passing a sample liquid through a liquid chromatography column, monitoring a liquid chromatography back pressure and varying a voltage applied to an Electrospray ionization source electrode in dependence upon said monitored liquid chromatography back pressure.

13 Claims, 1 Drawing Sheet

(56) References Cited

U.S. PATENT DOCUMENTS

| | | |
|---|---|---|
| 7,355,172 B2 | 4/2008 | Matsui et al. |
| 8,598,522 B2 | 12/2013 | Tomany et al. |
| 2005/0072915 A1 | 4/2005 | Stults et al. |

OTHER PUBLICATIONS

El-Faramawy, Ayman, K. W. Michael Siu, and Bruce A. Thomson. "Efficiency of nano-electrospray ionization." Journal of The American Society for Mass Spectrometry 16.10 (2005): 1702-1707.*

* cited by examiner

AUTOMATED ADJUSTMENT OF CAPILLARY VOLTAGE BASED ON THE ELUTION CONDITIONS TO RETAIN OPTIMAL IONIZATION CONDITIONS

CROSS REFERENCE TO RELATED APPLICATIONS

This application is the National Stage of International Application No. PCT/GB2014/052821, filed 17 Sep. 2014 which claims priority from and the benefit of United Kingdom patent application No. 1316686.3 filed on 20 Sep. 2013 and European patent application No. 13185285.7 filed on 20 Sep. 2013. The entire contents of these applications are incorporated herein by reference.

BACKGROUND OF THE PRESENT INVENTION

The present invention relates to a method of ionising a sample and an ionisation source. The preferred embodiment relates to a method of ionising an eluent emitted from a liquid chromatography source.

It is known to provide an Electrospray ionisation ("ESI") ion source which ionises eluent emitted from a Liquid Chromatography ("LC") source. The Electrospray ionisation ion source comprises a capillary tube which is maintained at a constant high voltage during the course of a liquid chromatography separation in order to cause eluent emerging from the liquid chromatography source to be ionised by the high voltage applied to the capillary tube.

Reverse phase liquid chromatography is well known and it is common to mix two solvents (A,B) which are then passed through a chromatography column. It is conventional to use water as the first solvent (A) and an organic solvent such as acetonitrile, methanol or propanol as the second solvent (B).

During the course of a liquid chromatography experiment it is known to progressively vary the ratio of the two solvents A,B whilst keeping the total flow rate constant. Varying the ratio of the two solvents A,B causes different species of analytes to elute from the chromatography column at different times. For example, it is known to progressively increase the percentage of the second organic solvent B from a few percent to e.g. 95-100% over the course of a few minutes.

It will be apparent, therefore, that during the course of a conventional liquid chromatography separation the chemical composition of the mobile phase will vary as the percentage of organic solvent is increased with time.

According to known methods the chemical composition of the mobile phase may change over a time period of e.g. 2+ minutes in the case of Ultra Performance Liquid Chromatography ("UPLC") (RTM) or over a longer time period of e.g. 7+ minutes for High Performance Liquid Chromatography ("HPLC").

Whilst the chemical composition of the mobile phase is being varied, the capillary voltage is maintained constant during an entire run per instrument polarity mode.

A problem with the known arrangement and method of operation is that the sensitivity can be compromised particularly if compounds or analytes of interest elute across the entire liquid chromatography gradient.

US2006/0118713 (Matsui) discloses a liquid chromatography/mass spectrometry apparatus comprising a liquid chromatography column coupled to an Electrospray ionisation source. Prior to analysis of a sample, a preparatory analysis step is carried out to investigate the relationship between solvent mixture ratio and optimal applied voltage. The results from the preparatory analysis are stored as a voltage data curve. When performing an analysis of a sample, the solvent mixture ratio is varied as a function of time. Each time the solvent mixture ratio is varied, the voltage data curve is used to determine an optimal voltage value to be applied to the ionisation probe.

It is desired to provide an improved ion source for a mass spectrometer and an improved method of ionising an eluent emitted from a liquid chromatography source.

SUMMARY OF THE PRESENT INVENTION

According to an aspect of the present invention there is provided a method of Electrospray ionisation comprising:

passing a sample liquid through a liquid chromatography column;

monitoring a liquid chromatography back pressure; and varying a voltage applied to an Electrospray ionisation source electrode in dependence upon the monitored liquid chromatography back pressure.

The preferred embodiment of the present invention relates to a method of Electrospray ionisation in which a sample liquid is passed through a liquid chromatography column before being introduced to and ionised by an Electrospray ionisation source. A particularly advantageous aspect of the present invention is that according to a preferred embodiment the voltage applied to the capillary of an Electrospray ionisation ion source is varied in order to maintain optimal ionization conditions throughout a liquid chromatography separation experiment.

The present invention results in a significant improvement in sensitivity compared with conventional arrangements wherein the capillary voltage is kept constant as the ratio of organic solvent to water is progressively increased with time.

According to the preferred embodiment, the back pressure of the liquid chromatography column is monitored and the voltage applied to the Electrospray ionisation source electrode is varied in dependence upon the monitored back pressure.

The Applicants have recognised the monitored back pressure of the liquid chromatography column provides a particularly convenient and advantageous basis on which to vary the voltage applied to the electrode.

In particular, the Applicants have recognised that as the back pressure is related to the viscosity of the solvent within the liquid chromatography column, by varying the voltage applied to the electrode in dependence upon the monitored back pressure, optimal ionization conditions can be maintained throughout a liquid chromatography separation experiment.

Varying the voltage applied to the Electrospray ionisation source electrode in dependence upon the monitored back pressure is also advantageous when compared with the method disclosed in US2006/0118713 (Matsui), for example, because the monitored back pressure effectively provides real-time information about the conditions within the liquid chromatography column.

Furthermore, the back pressure is typically already monitored in liquid chromatography systems to provide information regarding equilibrium, overpressure, etc. of the system and/or to facilitate the diagnosis of problems within the system. Furthermore, monitoring of the back pressure is also usually required in order to meet regulatory requirements.

Accordingly, a particular advantage of the present invention is that since the back pressure is normally monitored for other reasons, the present invention does not require the provision of additional sensors.

It will be appreciated therefore that the present invention provides an improved ion source.

In an embodiment the voltage is applied to the Electrospray ionisation source electrode in order to ionise the sample liquid.

In an embodiment the voltage is applied to a capillary of the Electrospray ionisation ion source, wherein the application of the voltage to the capillary ionises the sample liquid passing through and emerging from the capillary.

In an embodiment, the method further comprises:

pre-determining, predicting or estimating a relationship between the monitored liquid chromatography back pressure and an optimal value of the voltage for ionising a sample; and varying the voltage applied to the Electrospray ionisation source electrode in dependence upon the monitored liquid chromatography back pressure using the pre-determined, predicted or estimated relationship.

In an embodiment, the method further comprises:

determining a relationship between the monitored liquid chromatography back pressure and an optimal value of the voltage for ionising a sample during one or more initial liquid chromatography runs; and varying the voltage applied to the Electrospray ionisation source electrode in dependence upon the monitored liquid chromatography back pressure using the determined relationship during one or more subsequent liquid chromatography runs.

In an embodiment, the method further comprises:

determining a second different relationship between the monitored liquid chromatography back pressure and an optimal value of the voltage for ionising a sample during one or more liquid chromatography runs; and varying the voltage applied to the Electrospray ionisation source electrode in dependence upon the monitored liquid chromatography back pressure using the determined second relationship during one or more subsequent liquid chromatography runs.

According to another aspect of the present invention, there is provided a method of mass spectrometry comprising the method of Electrospray ionisation as described above.

According to another aspect of the present invention, there is provided an Electrospray ionisation system comprising:

a liquid chromatography column;

an Electrospray ionisation source; and a control system arranged and adapted:

(i) to monitor a liquid chromatography back pressure while a sample liquid is passed through the liquid chromatography column; and (ii) to vary a voltage applied to an electrode of the Electrospray ionisation source in dependence upon the monitored liquid chromatography back pressure.

In an embodiment, the voltage is applied to the electrode of the Electrospray ionisation source in order to ionise the sample liquid.

In an embodiment, the voltage is applied to a capillary of the Electrospray ionisation ion source, wherein the application of the voltage to the capillary ionises the sample liquid passing through and emerging from the capillary.

In an embodiment, the control system is arranged and adapted:

(i) to pre-determine, predict or estimate a relationship between the monitored liquid chromatography back pressure and an optimal value of the voltage for ionising a sample; and (ii) to vary the voltage applied to the Electrospray ionisation source electrode in dependence upon the monitored liquid chromatography back pressure using the pre-determined, predicted or estimated relationship.

In an embodiment, the control system is arranged and adapted:

(i) to determine a relationship between the monitored liquid chromatography back pressure and an optimal value of the voltage for ionising a sample during one or more initial liquid chromatography runs; and (i) to vary the voltage applied to the Electrospray ionisation source electrode in dependence upon the monitored liquid chromatography back pressure using the determined relationship during one or more subsequent liquid chromatography runs.

In an embodiment, the control system is arranged and adapted:

(i) to determine a second different relationship between the monitored liquid chromatography back pressure and an optimal value of the voltage for ionising a sample during one or more liquid chromatography runs; and (ii) to vary the voltage applied to the Electrospray ionisation source electrode in dependence upon the monitored liquid chromatography back pressure using the determined second relationship during one or more subsequent liquid chromatography runs.

According to another aspect of the present invention there is provided a mass spectrometer comprising the Electrospray ionisation system as described above.

In an embodiment, the system further comprises a pressure sensor for monitoring the liquid chromatography back pressure.

In an embodiment, the liquid chromatography column comprises: (i) a High-Performance Liquid Chromatography "HPLC" column; or (ii) an Ultra-Performance Liquid Chromatography "UPLC" (RTM) column.

In an embodiment, the liquid chromatography column has an internal diameter selected from the group consisting of: (i) <50 μm; (ii) 50-100 μm; (iii) 100-200 μm; (iv) 200-300 μm; (v) 300-400 μm; (vi) 400-500 μm; (vii) 500-600 μm; (viii) 600-700 μm; (ix) 700-800 μm; (x) 800-900 μm; (xi) 900-1000 μm; (xii) 1.0-1.5 mm; (xiii) 1.5-2.0 mm; (xiv) 2.0-2.5 mm; (xv) 2.5-3.0 mm; (xvi) 3.0-3.5 mm; (xvii) 3.5-4.0 mm; (xviii) 4.0-4.5 mm; (xix) 4.5-5.0 mm; (xx) 5.0-5.5 mm; (xxi) 5.5-6.0 mm; (xxii) 6.0-6.5 mm; (xxiii) 6.5-7.0 mm; (xxiv) 7.0-7.5 mm; (xxv) 7.5-8.0 mm; (xxvi) 8.0-8.5 mm; (xxvii) 8.5-9.0 mm; (xxviii) 9.0-9.5 mm; (xxix) 9.5-10.0 mm; and (xxx) >10.0 mm.

In an embodiment, the liquid chromatography column has a length selected from the group consisting of: (i) <10 mm; (ii) 10-20 mm; (iii) 20-30 mm; (iv) 30-40 mm; (v) 40-50 mm; (vi) 50-60 mm; (vii) 60-70 mm; (viii) 70-80 mm; (ix) 80-90 mm; (x) 90-100 mm; (xi) 100-110 mm; (xii) 110-120 mm; (xiii) 120-130 mm; (xiv) 130-140 mm; (xv) 140-150 mm; (xvi) 150-160 mm; (xvii) 160-170 mm; (xviii) 170-180 mm; (xix) 180-190 mm; (xx) 190-200 mm; (xxi) 200-210 mm; (xxii) 210-220 mm; (xxiii) 220-230 mm; (xxiv) 230-240 mm; (xxv) 240-250 mm; (xxvi) 250-260 mm; (xxvii) 260-270 mm; (xxviii) 270-280 mm; (xxix) 280-290 mm; (xxx) 290-300 mm; and (xxxi) >300 mm.

In an embodiment, the liquid chromatography column comprises C4, C8 or C18 stationary phase.

In an embodiment, the liquid chromatography column comprises particles having a size selected from the group consisting of: (i) <1 µm; (ii) 1-2 µm; (iii) 2-3 µm; (iv) 3-4 µm; (v) 4-5 µm; (vi) 5-6 µm; (vii) 6-7 µm; (viii) 7-8 µm; (ix) 8-9 µm; (x) 9-10 µm; (xi) 10-15 µm; (xii) 15-20 µm; (xiii) 20-25 µm; (xiv) 25-30 µm; (xv) 30-35 µm; (xvi) 35-40 µm; (xvii) 40-45 µm; (xviii) 45-50 µm; (xix) >50 µm.

In an embodiment, the liquid chromatography column comprises particles having a pore size selected from the group consisting of: (i) <10 nm; (ii) 10-20 nm; (iii) 20-30 nm; (iv) 30-40 nm; (v) 40-50 nm; (vi) 50-60 nm; (vii) 60-70 nm; (viii) 70-80 nm; (ix) 80-90 nm; (x) 90-100 nm; and (xi) >100 nm.

The system preferably further comprises a fluid delivery system for delivering the sample liquid to the liquid chromatography column.

The fluid delivery system preferably comprises an aqueous solvent or solution delivery device arranged and adapted to dispense an aqueous solvent or solution.

The fluid delivery system preferably comprises an organic solvent delivery device arranged and adapted to dispense an organic solvent.

The organic solvent is preferably selected from the group consisting of: (i) acetonitrile; (ii) methanol; (iii) propanol; (iv) an alcohol; and (v) tetrahydrofuran ("THF").

The fluid delivery system preferably comprises an analyte delivery device arranged and adapted to dispense an analyte.

The fluid delivery system is preferably arranged and adapted to mix the flows from the aqueous solvent or solution delivery device, the organic solvent delivery device and the analyte delivery device so as to provide an isocratic flow of the sample liquid to the liquid chromatography column.

In embodiment, the sample liquid is passed through the liquid chromatography column at a flow rate selected from the group consisting of: (i) <10 nl/min; (ii) 10-20 nl/min; (iii) 20-30 nl/min; (iv) 30-40 nl/min; (v) 40-50 nl/min; (vi) 50-60 nl/min; (vii) 60-70 nl/min; (viii) 70-80 nl/min; (ix) 80-90 nl/min; (x) 90-100 nl/min; (xi) 100-200 nl/min; (xii) 200-300 nl/min; (xiii) 300-400 nl/min; (xiv) 400-500 nl/min; (xv) 500-600 nl/min; (xvi) 600-700 nl/min; (xvii) 700-800 nl/min; (xviii) 800-900 nl/min; (xix) 900-1000 nl/min; (xx) 1-100 µl/min; (xxi) 100-200 µl/min; (xxii) 200-300 µl/min; (xxiii) 300-400 µl/min; (xxiv) 400-500 µl/min; (xxv) 500-600 µl/min; (xxvi) 600-700 µl/min; (xxvii) 700-800 µl/min; (xxviii) 800-900 µl/min; (xxix) 900-1000 µl/min; (xxx) 1.0-2.0 ml/min; (xxxi) 2.0-3.0 ml/min; (xxxii) 3.0-4.0 ml/min; (xxxiii) 4.0-5.0 ml/min; (xxxiv) 5.0-6.0 ml/min; (xxxv) 6.0-7.0 ml/min; (xxxvi) 7.0-8.0 ml/min; (xxxvii) 8.0-9.0 ml/min; (xxxviii) 9.0-10.0 ml/min; and (xxxix) >10.0 ml/min.

In embodiment, the sample liquid is passed through the liquid chromatography column with a substantially constant or regular flow.

According to an aspect of the present invention there is provided a method of ionising a sample comprising:

pre-determining, predicting or estimating how one or more chromatography parameters will vary during the course of an experimental acquisition; and then performing an experimental acquisition and during the course of the experimental acquisition varying one or more parameters of an ionisation source based upon the pre-determined, predicted or estimated variation of the one or more chromatography parameters.

The step of pre-determining, predicting or estimating how one or more chromatography parameters will vary during the course of an experimental acquisition preferably comprises pre-determining, predicting or estimating how the one or more chromatography parameters will vary as function of time.

The one or more chromatography parameters preferably comprise one or more liquid chromatography parameters.

The one or more chromatography parameters are preferably selected from the group comprising: (i) flow rate; (ii) time; (iii) mobile phase composition; (iv) pH; (v) viscosity; (vi) surface tension; (vii) conductivity; (viii) chemical composition of a mobile phase; (ix) ratio of a first solvent to a second solvent; and (x) percentage concentration of an organic solvent.

According to a less preferred embodiment the one or more chromatography parameters may comprise one or more gas chromatography parameters.

According to another embodiment the one or more chromatography parameters may relate to either: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The one or more parameters of the ionisation source preferably relate to a voltage applied to the ionisation source in order to ionise a sample.

The ionisation source preferably comprises an Electrospray ionisation ion source. The one or more parameters preferably relate to a voltage applied to a capillary of the Electrospray ionisation ion source, wherein the application of the voltage to the capillary preferably ionises a sample passing through and emerging from the capillary.

According to a less preferred embodiment the one or more parameters of the ionisation source may relate to a probe distance, a probe height, a liquid flow rate, a nebuliser gas flow rate of the ionisation source or a temperature of a gas used to desolvate the sample.

According to another aspect of the present invention there is provided an ionisation source comprising:

a control system arranged and adapted:

(i) to pre-determine, predict or estimate how one or more chromatography parameters will vary during the course of an experimental acquisition; and then (ii) to perform an experimental acquisition and during the course of the experimental acquisition vary one or more parameters of the ionisation source based upon the pre-determined, predicted or estimated variation of the one or more chromatography parameters.

The control system is preferably arranged and adapted to pre-determine, predict or estimate how one or more chromatography parameters will vary during the course of an experimental acquisition by pre-determining, predicting or estimating how the one or more chromatography parameters will vary as function of time.

The one or more chromatography parameters preferably comprise one or more liquid chromatography parameters.

The one or more chromatography parameters are preferably selected from the group comprising: (i) flow rate; (ii) time; (iii) mobile phase composition; (iv) pH; (v) viscosity; (vi) surface tension; (vii) conductivity; (viii) chemical composition of a mobile phase; (ix) ratio of a first solvent to a second solvent; and (x) percentage concentration of an organic solvent.

According to a less preferred embodiment the one or more chromatography parameters may comprise one or more gas chromatography parameters.

According to another embodiment the one or more chromatography parameters may relate to either: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The one or more parameters of the ionisation source preferably relate to a voltage applied to the ionisation source in order to ionise a sample.

The ionisation source preferably comprises an Electrospray ionisation ion source.

The one or more parameters preferably relate to a voltage applied to a capillary of the Electrospray ionisation ion source, wherein the application of the voltage to the capillary ionises a sample passing through and emerging from the capillary.

According to a less preferred embodiment the one or more parameters of the ionisation source may relate to a probe distance, a probe height, a liquid flow rate, a nebuliser gas flow rate of the ionisation source or a temperature of a gas used to desolvate the sample.

A particularly advantageous aspect of the present invention is that according to a preferred embodiment the voltage applied to the capillary of an Electrospray ionisation ion source is varied in order to maintain optimal ionization conditions throughout a liquid chromatography separation experiment. The capillary voltage is preferably varied based upon the predicted variation of one or more key liquid chromatography parameters such as the ratio of organic solvent to water ("% organic").

The present invention results in a significant improvement in sensitivity compared with conventional arrangements wherein the capillary voltage is kept constant as the ratio of organic solvent to water is progressively increased with time.

The preferred embodiment relates to maintaining an optimum capillary voltage across a liquid chromatography run based on the liquid chromatography conditions regardless of what is being monitored by the mass spectrometer. This is possible because of the slower timescales of the liquid chromatography gradient (typically a few minutes).

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The mass spectrometer may comprise a chromatography detector.

The chromatography detector may comprise a destructive chromatography detector preferably selected from the group consisting of: (i) a Flame Ionization Detector ("FID"); (ii) an aerosol-based detector or Nano Quantity Analyte Detector ("NQAD"); (iii) a Flame Photometric Detector ("FPD"); (iv) an Atomic-Emission Detector ("AED"); (v) a Nitrogen Phosphorus Detector ("NPD"); and (vi) an Evaporative Light Scattering Detector ("ELSD").

Additionally or alternatively, the chromatography detector may comprise a non-destructive chromatography detector preferably selected from the group consisting of: (i) a fixed or variable wavelength UV detector; (ii) a Thermal Conductivity Detector ("TCD"); (iii) a fluorescence detector; (iv) an Electron Capture Detector ("ECD"); (v) a conductivity monitor; (vi) a Photoionization Detector ("PID"); (vii) a Refractive Index Detector ("RID"); (viii) a radio flow detector; and (ix) a chiral detector.

The ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to an embodiment analyte ions may be subjected to Electron Transfer Dissociation ("ETD") fragmentation in an Electron Transfer Dissociation fragmentation device. Analyte ions are preferably caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) C60 vapour or atoms; and (viii) magnesium vapour or atoms.

The multiply charged analyte cations or positively charged ions preferably comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to a particularly preferred embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments of the present invention will now be described, by way of example only, and with reference to the accompanying drawing in which.

DETAILED DESCRIPTION OF PREFERRED EMBODIMENTS

A preferred embodiment of the present invention will now be described with reference to FIG. 1.

According to an embodiment of the present invention an Electrospray Ionisation ("ESI") ion source is provided together with a control system which includes a look-up table. The Electrospray Ionisation ion source includes a capillary and is preferably coupled to a liquid chromatography separator.

The liquid chromatography separator preferably supplies an eluent to the Electrospray Ionisation ion source and the Electrospray Ionisation ion source preferably ionises the eluent which emerges from the liquid chromatography device.

The look-up table preferably includes details of how the voltage applied to the capillary of the Electrospray ionisation ion source should be varied, preferably increased, as a function of time in a coordinated manner with, for example, increasing the percentage of organic solvent in the mobile phase which is supplied to the liquid chromatography separator.

The control system preferably utilises the look-up table to change or otherwise alter the capillary voltage applied to the Electrospray ionisation ion source throughout or during the course of a single liquid chromatography run, separation or acquisition.

The capillary voltage look-up table may be created manually.

Alternatively, the capillary voltage look-up table may be created automatically based upon the liquid chromatography conditions.

Table 1 as shown below illustrates an embodiment of the present invention wherein the ratio of organic solvent to water ("% organic") of a liquid chromatography separator was pre-arranged to vary as a function of time and illustrates how the capillary voltage applied to the Electrospray ionisation ion source may be arranged to vary as a function of time in close relationship to the pre-arranged variation in the concentration of the organic solvent.

TABLE 1

| Time (mins) | % Organic | Capillary Voltage (V) |
| --- | --- | --- |
| 0 | 5% | 800 |
| 0.3 | 5% | 800 |
| 1.5 | 95% | 3000 |
| 2.3 | 95% | 3000 |
| 2.5 | 5% | 800 |
| 3 | 5% | 800 |

Figure 1:
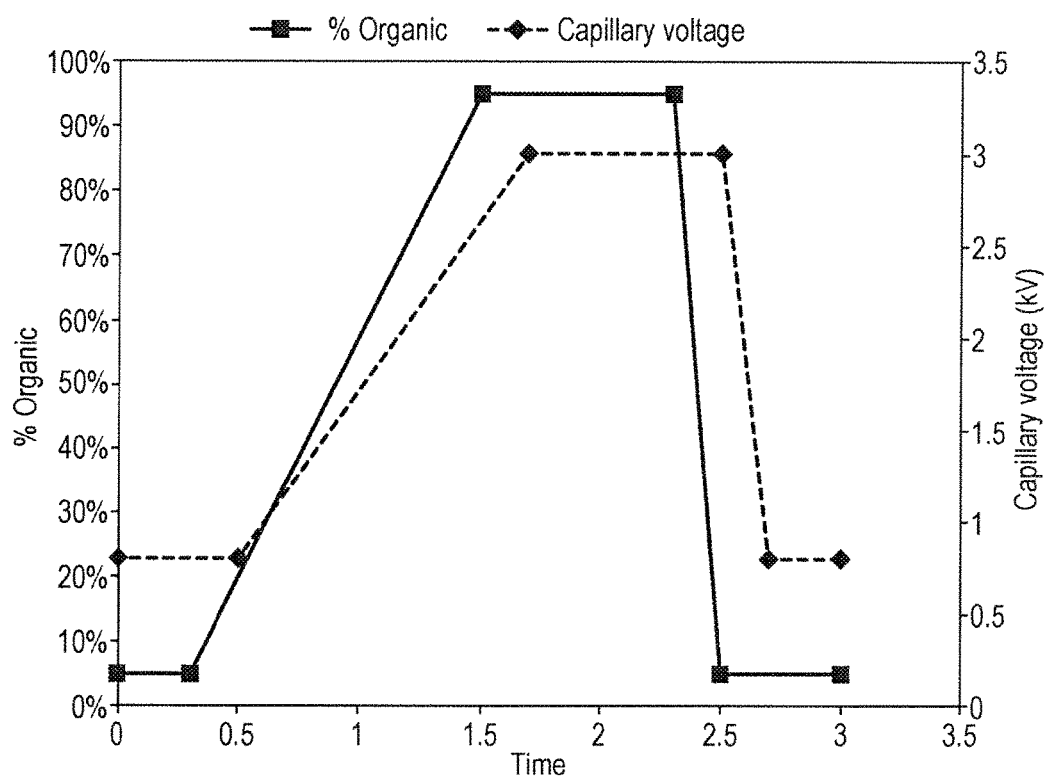
FIG. 1 illustrates how according to a preferred embodiment of the present invention the voltage applied to the capillary of an Electrospray ionisation ion source is progressively increased in a similar manner to a change in the ratio of an organic solvent to water of a mobile phase which is passed through a liquid chromatography separation device arranged upstream of the Electrospray ionisation ion source.

FIG. 1 illustrates an embodiment of the present invention wherein the percentage of organic solvent and the applied capillary voltage were varied in a very similar manner to that illustrated by Table 1 above.

It will be apparent from FIG. 1 that the change of the capillary voltage may be arranged so as to lag slightly behind the gradient change in order to take into account the time taken for the mixture of solvents to reach the ion source. According to an embodiment this delay may be incorporated automatically. However, it is not essential that the variation in the voltage applied to the Electrospray ion source lags behind the change in the concentration of the organic solvent of the mobile phase.

According to other embodiments the capillary voltage or another parameter of the ion source may be changed based on one or more of the following parameters: (i) mobile phase flow rate; (ii) time; (iii) mobile phase composition including percentage organic and percentage aqueous; (iv) pH; (v) viscosity; (vi) surface tension; and (vii) conductivity.

Although above preferred embodiment has been described in terms of varying a capillary voltage as a function of time in a coordinated manner with increasing the percentage of organic solvent in the mobile phase which is supplied to the liquid chromatography separator, according to a more preferred embodiment the back pressure of the liquid chromatography column is preferably monitored. According to a particularly preferred embodiment the capillary voltage is varied in dependence upon the monitored liquid chromatography back pressure.

Figure 2:
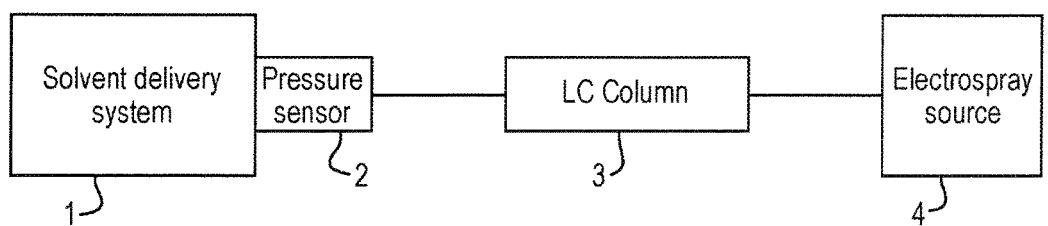
FIG. 2 schematically shows a liquid chromatography system in accordance with an embodiment of the present invention.

FIG. 2 illustrates a liquid chromatography system in accordance with this preferred embodiment. The liquid chromatography system preferably comprises a solvent or fluid delivery system 1, a pressure sensor 2, a liquid chromatography (LC) column 3 and an Electrospray ionisation source 4.

In use, the solvent delivery system 1 preferably delivers a sample liquid to the liquid chromatography column 3. The sample liquid preferably comprises an aqueous solvent or solution, an organic solvent such as acetonitrile, methanol or propanol, and an analyte. The pressure sensor 2 is preferably arranged and adapted to monitor the back pressure of the liquid chromatography column 3 as the sample liquid is passed though the liquid chromatography column 3. The sample liquid is preferably passed to the Electrospray ionisation source 4 as it elutes from the liquid chromatography column 3, and is preferably ionised by the Electrospray ionisation source 4.

The monitored back pressure is preferably used to provide information regarding equilibrium, overpressure, etc. of the LC system and/or to facilitate the diagnosis of problems within the LC system. According to the preferred embodiment, the monitored back pressure is also used to determine the optimal voltage that should be applied to the capillary of the Electrospray ionisation source 4 so as to maintain optimal ionization conditions, e.g. throughout a liquid chromatography separation experiment.

For a simple tube, the back pressure or change in pressure $\Delta P$ of a liquid chromatography column can be calculated by the Poiseuille equation:

$$\Delta P = 8\eta l Q / \pi r^4 \quad (1)$$

wherein $\eta$ is the viscosity of the sample liquid, l is the length of the tube, Q is the flow rate of the sample liquid and r is the radius of the tube.

Since the back pressure $\Delta P$ is related to the viscosity $\eta$ of the sample liquid within the liquid chromatography column 3, which is in turn related to the composition (i.e. solvent ratio) of the sample liquid, by varying the capillary voltage in dependence upon the monitored back pressure optimal ionisation conditions can be maintained throughout a liquid chromatography separation experiment.

As will be appreciated from Eqn. 1, the relationship between the back pressure and the viscosity applies for any constant flow rate and thus the present invention is applicable over the entire range of liquid chromatography flow rates (e.g. flow rates of nL/min, µL/min, mL/min, etc.).

Varying the capillary voltage in dependence upon the monitored back pressure is advantageous because the monitored back pressure effectively provides direct, real-time information about the conditions within the liquid chromatography column 3 during an LC run.

Furthermore, the back pressure will typically already be monitored in liquid chromatography systems, e.g. to provide information regarding equilibrium, overpressure, etc. of the system and/or to facilitate the diagnosis of problems within the system, so that it is not necessary to provide additional sensors (e.g. over and above the pressure sensor 2 which is typically already present in a liquid chromatography system) for the monitoring.

In one embodiment, the relationship between the monitored back pressure and the applied capillary voltage is fixed e.g. by an initial calibration run, and used for all experimental runs.

In another embodiment, the relationship between the monitored back pressure and the applied capillary voltage may be periodically updated e.g. by periodically performing a calibration run.

According to a particularly preferred embodiment, the relationship is set based on a first LC run or a calibration or set-up run that is performed for or during a particular set of experiments (the set of experiments may comprises, for example, a plurality of LC runs that are performed using the same or similar LC methods or conditions). That is, the relationship between the monitored back pressure and the applied capillary voltage is preferably determined before or during each set of LC experiments, and the determined relationship is then preferably used for all LC experiments performed during that set of LC experiments. Advantageously, this can avoid problems associated with the back pressure changing as the liquid chromatography column 3 ages.

Although the preferred embodiment relates to varying the voltage applied to a capillary of an Electrospray Ionisation ion source, e.g. in dependence upon the change in percentage solvent of the mobile phase which is pumped through a liquid chromatography column as a function of time, other embodiments are also contemplated wherein another parameter of the ion source may be varied such as the probe distance, the probe height, a liquid flow rate or a nebuliser gas flow rate.

Although the present invention has been described with reference to preferred embodiments, it will be understood by those skilled in the art that various changes in form and detail may be made without departing from the scope of the invention as set forth in the accompanying claims.

The invention claimed is:

1. A method of Electrospray ionisation comprising:
   passing a sample liquid through a liquid chromatography column;
   monitoring a liquid chromatography back pressure; and
   varying a voltage applied to an Electrospray ionisation source electrode in dependence upon said monitored liquid chromatography back pressure.

2. A method as claimed claim 1, wherein said voltage is applied to said Electrospray ionisation source electrode in order to ionise said sample liquid.

3. A method as claimed in claim 1, wherein said voltage is applied to a capillary of said Electrospray ionisation ion source, wherein the application of said voltage to said capillary ionises said sample liquid passing through and emerging from said capillary.

4. A method as claimed in claim 1, further comprising:
   pre-determining, predicting or estimating a relationship between said monitored liquid chromatography back pressure and an optimal value of said voltage for ionising a sample; and
   varying said voltage applied to said Electrospray ionisation source electrode in dependence upon said monitored liquid chromatography back pressure using said pre-determined, predicted or estimated relationship.

5. A method as claimed in claim 1, further comprising:
   determining a relationship between said monitored liquid chromatography back pressure and an optimal value of said voltage for ionising a sample during one or more initial liquid chromatography runs; and
   varying said voltage applied to said Electrospray ionisation source electrode in dependence upon said monitored liquid chromatography back pressure using said determined relationship during one or more subsequent liquid chromatography runs.

6. A method as claimed in claim 5, further comprising:
   determining a second different relationship between said monitored liquid chromatography back pressure and an optimal value of said voltage for ionising a sample during one or more liquid chromatography runs; and
   varying said voltage applied to said Electrospray ionisation source electrode in dependence upon said monitored liquid chromatography back pressure using said determined second relationship during one or more subsequent liquid chromatography runs.

7. A method of mass spectrometry comprising a method of Electrospray ionisation comprising:
   passing a sample liquid through a liquid chromatography column;

monitoring a liquid chromatography back pressure; and
varying a voltage applied to an Electrospray ionisation source electrode in dependence upon said monitored liquid chromatography back pressure.

8. An Electrospray ionisation system comprising:
a liquid chromatography column;
an Electrospray ionisation source; and
a control system arranged and adapted:
(i) to monitor a liquid chromatography back pressure while a sample liquid is passed through said liquid chromatography column; and
(ii) to vary a voltage applied to an electrode of said Electrospray ionisation source in dependence upon said monitored liquid chromatography back pressure.

9. An Electrospray ionisation system as claimed in claim 8, wherein said voltage is applied to said electrode of said Electrospray ionisation source in order to ionise said sample liquid.

10. An Electrospray ionisation system as claimed in claim 8, wherein said voltage is applied to a capillary of said Electrospray ionisation source, wherein the application of said voltage to said capillary ionises said sample liquid passing through and emerging from said capillary.

11. An Electrospray ionisation system as claimed in claim 8, wherein said control system is arranged and adapted:
(i) to pre-determine, predict or estimate a relationship between said monitored liquid chromatography back pressure and an optimal value of said voltage for ionising a sample; and
(ii) to vary said voltage applied to said Electrospray ionisation source electrode in dependence upon said monitored liquid chromatography back pressure using said pre-determined, predicted or estimated relationship.

12. An Electrospray ionisation system as claimed in claim 8, wherein said control system is arranged and adapted:
(i) to determine a relationship between said monitored liquid chromatography back pressure and an optimal value of said voltage for ionising a sample during one or more initial liquid chromatography runs; and
(ii) to vary said voltage applied to said Electrospray ionisation source electrode in dependence upon said monitored liquid chromatography back pressure using said determined relationship during one or more subsequent liquid chromatography runs.

13. An Electrospray ionisation system as claimed in claim 12, wherein said control system is arranged and adapted:
(i) to determine a second different relationship between said monitored liquid chromatography back pressure and an optimal value of said voltage for ionising a sample during one or more liquid chromatography runs; and
(ii) to vary said voltage applied to said Electrospray ionisation source electrode in dependence upon said monitored liquid chromatography back pressure using said determined second relationship during one or more subsequent liquid chromatography runs.

* * * * *